(12) United States Patent
Sukumar

(10) Patent No.: US 8,221,684 B2
(45) Date of Patent: Jul. 17, 2012

(54) MOBILE INTRA-OPERATIVE MICROSCOPIC DIAGNOSIS LABORATORY

(76) Inventor: V. Raman Sukumar, Lewes, DE (US)

( * ) Notice: Subject to any disclaimer, the term of this patent is extended or adjusted under 35 U.S.C. 154(b) by 1006 days.

(21) Appl. No.: 12/228,743

(22) Filed: Aug. 15, 2008

(65) Prior Publication Data
US 2010/0041094 A1 Feb. 18, 2010

(51) Int. Cl.
*G01N 15/06* (2006.01)
(52) U.S. Cl. ............. 422/68.1; 422/63; 422/64; 422/65; 422/67; 422/500; 422/501; 436/180; 296/24.3
(58) Field of Classification Search .......... 422/500–502, 422/63–65, 67, 68.1; 436/180; 296/24.1, 296/24.3
See application file for complete search history.

(56) References Cited

U.S. PATENT DOCUMENTS 6,082,799 A * 7/2000 Marek ..................... 296/24.38
6,536,219 B2 * 3/2003 Peters ............................ 62/62

* cited by examiner

Primary Examiner — Jyoti Nagpaul
(74) Attorney, Agent, or Firm — John C. Andrade; Parkowski, Guerke & Swayze, P.A.

(57) ABSTRACT

A mobile intra-operative microscopic diagnosis laboratory capable of analyzing fresh tissue specimens and providing intra-operative consultation within 20 minutes is described. The mobile laboratory is preferably a van and contains a cryostat for freezing the fresh tissue specimens and a means for cutting the specimens. In addition, it also contains the means for reading the slides to make microscopic diagnosis and a means for handling for fresh tissue and a means for indicating various locations in the specimen, preferably by inking them. It preferably contains a stainer for staining the samples and an intercom for communicating the microscopic diagnosis back to the operating room.

1 Claim, 5 Drawing Sheets

MOBILE INTRA-OPERATIVE MICROSCOPIC DIAGNOSIS LABORATORY

BACKGROUND OF THE INVENTION

1. Field of the Invention

This invention relates to a mobile laboratory to provide intra-operative microscopic diagnosis.

2. Description of Prior Art

Traditionally invasive procedures (surgeries, CAT scan directed biopsies, etc.) requiring intra-operative consultation (IOC) from a pathologist, are taken to the hospital, even if these can be performed in physicians' offices. This is because, hospitals where most invasive procedures are performed, are where pathology practices are centered. Typically physicians' offices and small surgery centers would not have the services of a pathologist available for IOC. There is a need for IOC to be available for small surgery centers and to physicians' offices. Currently, once a fresh tissue specimen is taken from the patient if the surgery is performed in a physicians' office or in a small surgery center, then the surgery must be halted until the analysis of the fresh tissue specimen can be completed. This would typically involve transportation to a hospital where pathologist services are available and could either take hours or sometime the continuation of the surgery is rescheduled for a later day.

Providing mobile ambulatory surgical centers such as those disclosed in U.S. Pat. No. 6,082,799 are known and performing freezing operations in a vehicle are also well known. However, none of the operations or mobile medical vehicles available are capable of providing intra-operative microscopic diagnosis capable of analyzing fresh tissue specimens and providing intra-operative consultation within twenty minutes. Given the exploding number of smaller surgical procedures being performed outside hospitals, the need for such a method and vehicle for providing such diagnosis. The object of this invention is to provide a method and mobile laboratory capable of being utilized to analyze fresh tissue specimens and providing intra-operative consultation within twenty minutes. It is the further object of this advantage to do so in a manner that complies with all OSHA and Clinical Laboratory Improvements Act of 1988 (CLIA) Requirements for the handling of tissue specimens.

SUMMARY OF THE INVENTION

The present invention includes a Mobile Intra-Operative Microscopic Diagnosis Laboratory capable of being utilized to analyze fresh tissue specimens and provide intra-operative consultation within twenty minutes. The laboratory is mobile and while preferably a van, includes any means for transporting said laboratory from location to location. In handling the fresh tissue specimens it is necessary to have a means for freezing said fresh tissue specimens. Currently the preferable way of freezing the fresh tissue specimens is with a cryostat. It is also necessary to have a means within said laboratory for reading slides to make a microscopic diagnosis, typically utilizing a microscope. It is very important that there be sufficient means within said laboratory for handling the fresh tissue specimens. Typically they would be handled with non-porous gloves and the surfaces the fresh tissue specimens are on would be non-porous surfaces. There would also need to be a means to dispose of all the fresh tissue specimens and contaminated material, which would include biohazardous waste disposal and would also include gloves, masks, plastic aprons, etc. pursuant to OSHA Regulations. All the operations within said laboratory would be covered by the Clinical Laboratories Improvements Act of 1988 which governs the handling of fresh tissue specimens.

There would need to be a means within said laboratory for indicating the various locations in fresh tissue specimens and this would preferably be by inking said tissue specimens. It would also be necessary for there to be a means within the laboratory for dissecting the fresh tissue specimens and this would typically include cutting with a knife, blade or scalpel. The preferred way would be as shown in the drawings by use of a special knife within the cryostat so that after freezing the tissue specimens could be cut to some very thin thicknesses (4-5 microns thick). After the fresh tissue specimen is frozen it is preferable to have a means within said laboratory for histological staining of the specimen. It is also preferable within said laboratory for means for communicating microscopic diagnosis to an outside entity, for example an intercom system with a wireless connection directly to the operating room.

The present invention further includes a method for analyzing fresh tissue specimens and providing intra-operative consultation within twenty minutes within a Mobile Intra-Operative Microscopic Diagnosis Laboratory, when the laboratory can be transported from location to location. Included are handling the fresh tissue specimens, making microscopic diagnosis, indicating various locations in the fresh tissue specimens, dissecting said specimens, freezing said specimens, and identifying each specimen by giving it a unique number. It is also necessary to provide heating and cooling within the laboratory without creating unnecessary vibration so that the pathologist within the laboratory can read the specimens. It is further preferable to have an automatic stainer within the laboratory for staining of the fresh tissue specimens after being frozen.

MICS (mobile intra-operative consultation service) facilitates disconnecting the surgeries connected to the hospitals by IOC. In the process it helps the changing paradigm of reducing health care costs, improving community based healthcare services and patient convenience. In this changing paradigm of striving to decrease healthcare costs, some of the more expensive hospital based services have begun to be outsourced (generic drugs, home-health care, alternative medicine, birth centers, non-physician healthcare providers, minor invasive procedures, etc.) Three of these are centered around services provided by the pathologists.

The most important of the latter relates to the surgeries that can be performed in offices and in ambulatory surgery centers (ASCs) which will be followed by the invasive procedures being performed by radiologists and will finally lead to office based pathology service for hospitals.

The present invention has adapted resources to provide the intra-operative consultation outside the hospital. MICS is the first accredited mobile intra-operative consultation service; it is equipped with all of the gadgets, the information and the telecommunication system required by various regulatory authorities and is operated under strict SOP. Physicians and patients have the convenience of having minor surgeries (not major ones requiring open abdominal/thoracic surgeries and not for high risk patients), which constitute about a third of the hospital surgical volume, to be performed in offices and ASCs. The MICS is driven to the location by the pathologist to provide the required intra-operative consultation (diagnosis of a lesion required to direct the further course of action or consultation on complete removal of a previously diagnosed lesion or providing a means to harvest tissue for highly specialized studies, etc.) Hospital based surgeries are not only expensive but cause tremendous inconvenience to patients, requiring arrangements for child-care, scheduling time off (paid or unpaid) from work or school, etc. MICS addresses both by reducing the cost by over 75% and facilitating the convenience of adjusting healthcare to the patient's daily routine. ASC or office based procedures take much less time and can be centered around patient convenience; even over the weekend.

The next step would be to provide the same for the radiologists who perform biopsies of internal organs by introducing needles under the guidance of a CAT scan. Pathologist will ensure adequacy of the material obtained by this expensive procedure, which can now be performed in outpatient radiology facilities. The cost and convenience of this process is similar to the above.

The final step will be complete out sourcing of the pathology services. Most pathologists are based in hospitals mainly to provide intra-operative consultations. Other services provided by the pathologists include postmortem examination, diagnosis on other tissues removed and medical directorship of the clinical laboratory. All of the latter can be provided by on-call pathologists and/or outside the hospital. Traditionally most hospitals employ the pathologists and provide them with prime-space. With introduction of DRG, laboratories are a cost-center (not a revenue center) for hospitals. By out sourcing the pathology services, pathologists can provide the service on a contract basis and earn most of their income from outpatient surgeries which generally do not come to hospitals. This is very economical for hospitals by saving space and not having to employ pathologists.

The MICS provides the passport to the outside world and cuts the cord that attaches the expensive services to the hospital. It helps the surgeons and the radiologists to be more efficient and entrepreneurial. It helps the hospitals focus on the major surgeries with better utilization of their resources during this drought—shortage of health care workers. It improves community based pathology service, which is non-existent at this time. It helps patient morale and economics. It is an important conduit to improved healthcare in America.

DETAILED DESCRIPTION OF A PREFERRED EMBODIMENT

Figure 1:
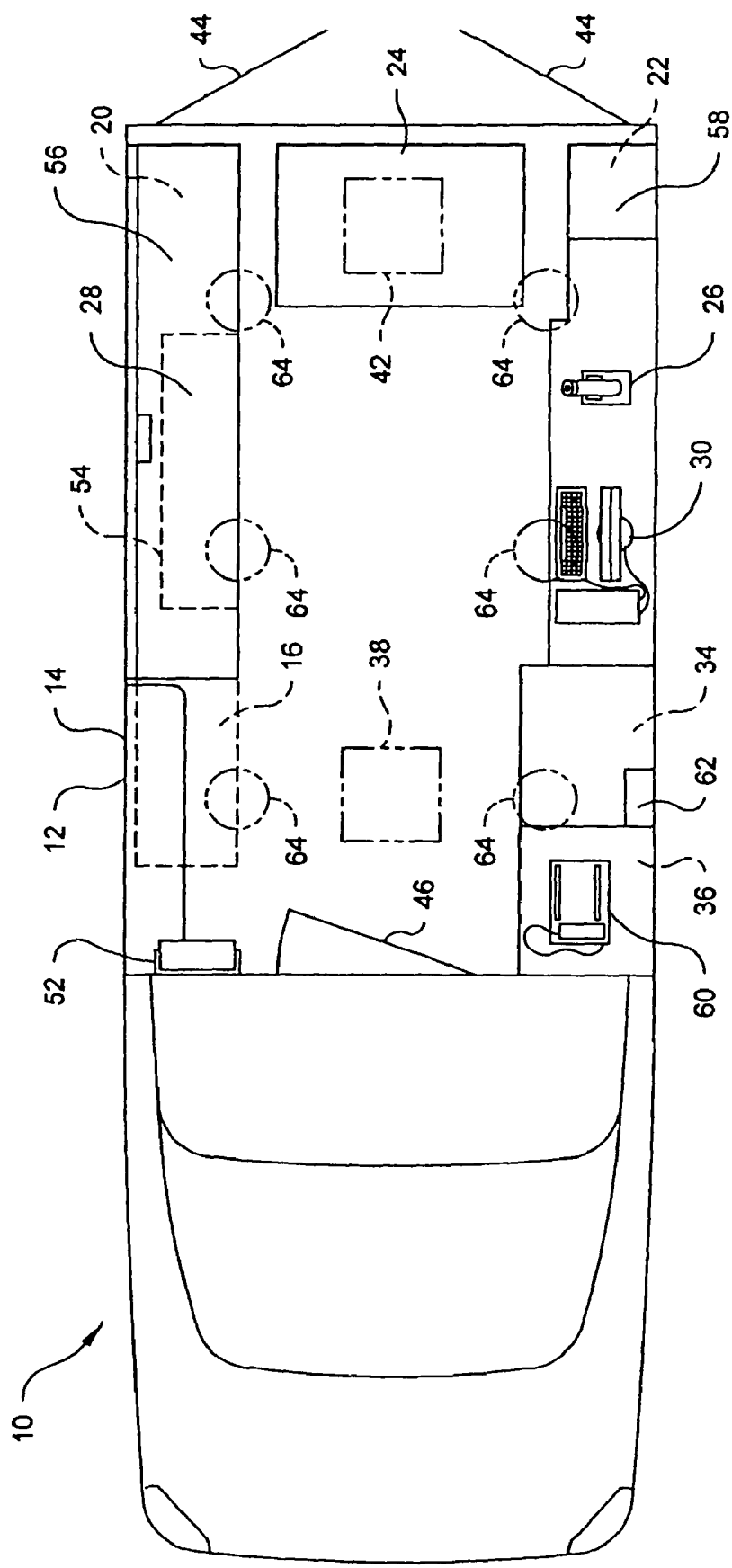
FIG. 1 is a top view schematic of the inside of the van of the present invention.
Figure 3:
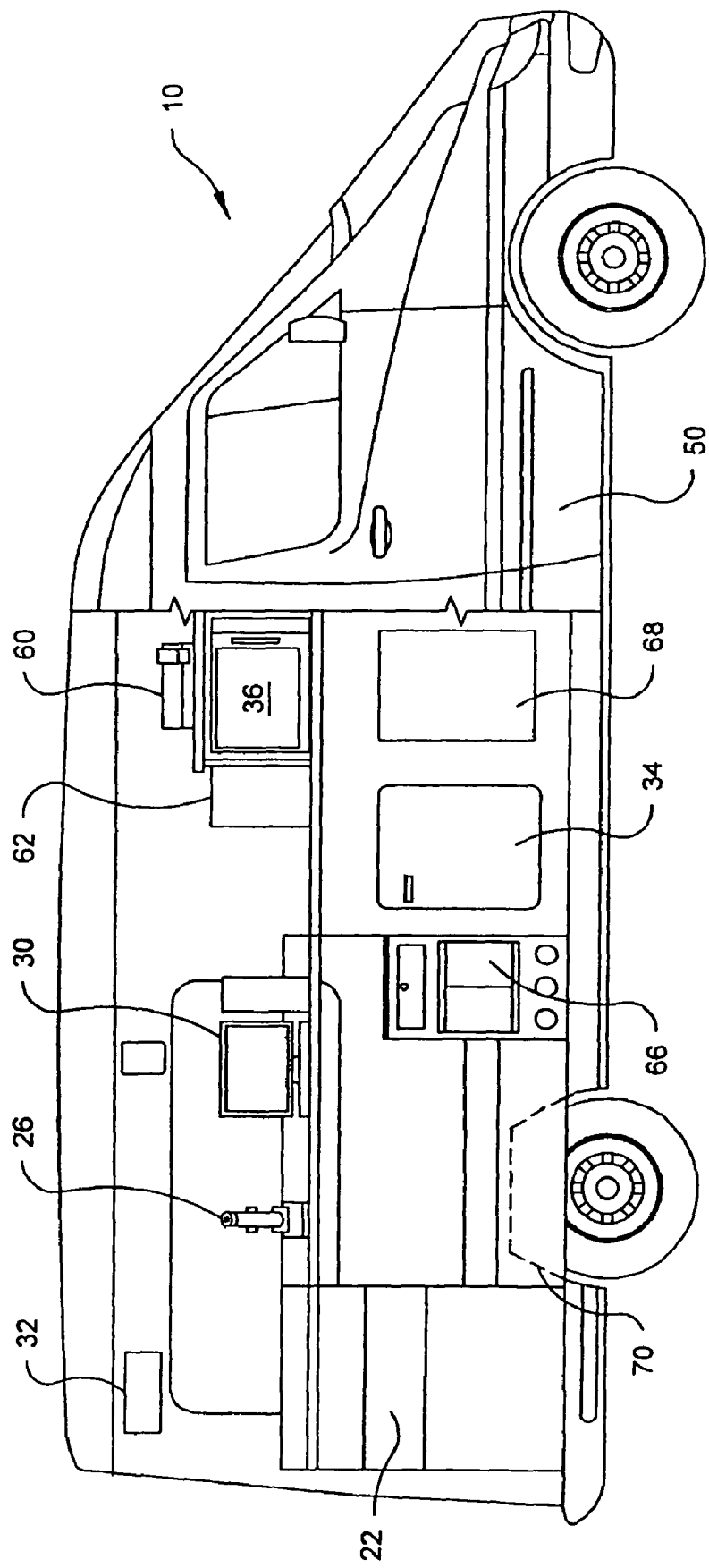
FIG. 3 is an exposed driver's side view of the van of the present invention.

FIG. 1 is a top view schematic of the inside of the Mobile Intra-Operative Microscopic Diagnosis Laboratory. Shown in FIG. 1 is a van 10 which is the most likely means for transporting the laboratory. The best way of explaining the schematic is to describe the process that the physician receiving the sample would go through in providing the diagnosis. The sample is typically first received through the window 14 which is in the upper portion of the sliding door 12. A fold over counter top 16 is available to be utilized when the sample is received. The first step after receiving the sample is the grossing step where the sample is measured, described and inked typically at the fold over counter top or grossing station 16, which is all dictated by the physician. Next, the sample is placed on the chuck 82, shown in FIG. 4, which is part of the cryostat 24 and then the chuck 82 is placed inside the cryostat 24. After the sample is frozen within the cryostat 24, microscopic sections of the sample are cut and placed on a slide. Not all, but many samples are then stained in the stainer 28 for approximately 35 seconds and then the physician takes the sample and places it under the microscope 26. After examining the sample under the microscope 26, the physician then makes the diagnosis and communicates the diagnosis with the surgeon in the operating room. Communication with the surgeon is preferably by an intercom to the operating room. The physician in the operating room will preferably be given one intercom and its mate will be the intercom 32, as shown in FIG. 3, located preferably above the microscope 26. In making the diagnosis, the physician will preferably use a unique identification number, which is compiled by entering the Social Security number and date of birth of the patient, which gives the identification number unique to that particular patient. After the diagnosis is made and communicated to the operating physician, the physician in the laboratory will dictate the diagnosis into the digital dictation system, which is part of the computer 30 as shown in FIG. 3. A combination printer, fax machine and scanner 60 is provided near the front of the laboratory as shown.

The Mobile Intra-Operative Microscopic Diagnosis Laboratory shown in FIG. 1 also contains numerous items that aid the pathologist in performing the tissue analysis. The van must be well lit as shown by the lights 64 at the top of the van. A paper towel holder 52 is placed as shown for the convenience of the physician. Additional curbside storage cabinets 54 are included under the stainer 28 and a counter 56 on top of the left battery and a counter 58 on top of the right battery provide more workspace.

Proper air conditioning is critical to maintaining and operating the laboratory. An earlier design of the present invention included the air conditioning running off the van's diesel engine. The problem was that the vibration was so great that the slides could not be read. The solution was to put in a separate air conditioning and heating unit that cooled and heated the lab without running the engine and thus without causing vibration. The air conditioning runs off of the left battery 20 and the right battery 22. To recharge the batteries a car plug can be added outside the van and a generator can sit next to the van providing the air conditioning and heating. The generator can run on gasoline and be attached to the back of the van. The roof air conditioning unit 38 is designed to produce adequate cooling. There is also a roof vent 42. Additional access and exit points are provided by the rear doors 44 and front doors 46 as shown in FIG. 1.

Figure 2:
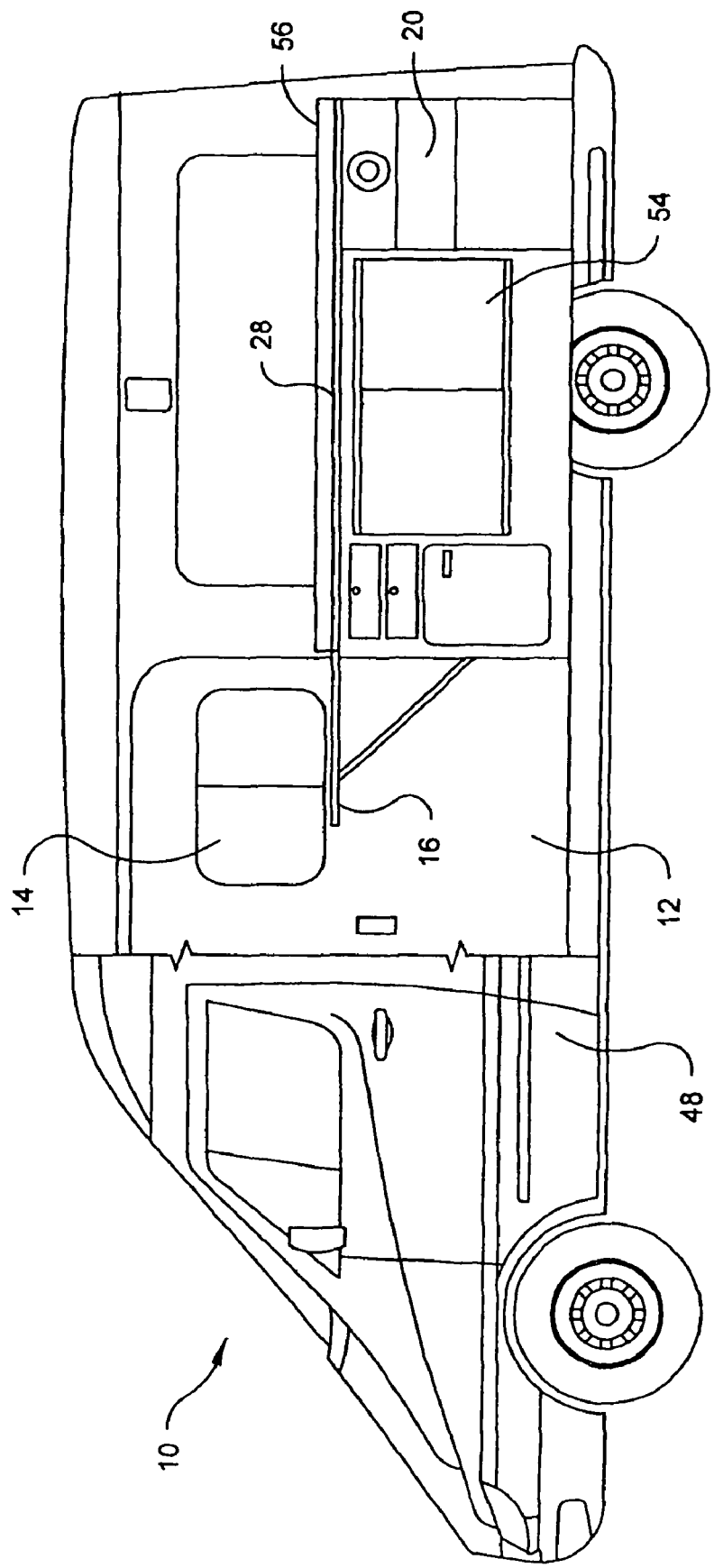
FIG. 2 is an exposed curbside view of the van of the present invention.

FIG. 2 is an exposed curbside view of the van of the present invention. FIG. 2 shows the driver door 48 and then looks through the van to the curbside looking at the curbside from the perspective of someone inside the van. The side entry door 12 is the primary means that the pathologist would enter and exit the laboratory. Once entering the laboratory, the flipdown corner top and grossing station 16 would be set in place which is right below the slider window 14. This window 14 is primarily where the tissue samples would be received from. The grossing station 16 would be the first operation where the samples are received and to the right of the grossing station 16 is the stainer 28. There are extensive batteries necessary for the operation of the laboratory and shown on the curbside in FIG. 2 is the left battery 20. From the pathologist's view if one were to continue working around the van clockwise, at the rear of the van would be the cryostat 24 shown in FIG. 1 and FIG. 4.

The driver's side of the van is shown in FIG. 3, and as in FIG. 2, here the passenger door 50 is shown and we are looking through the van to the driver's side. Continuing on in clockwise fashion, is the right battery 22 and sitting near the top of the van, spatially above the battery would be the intercom 32. Proceeding next around the van would be the microscope 26 and next to that would be the computer 30. The computer would sit on top of the slide storage cabinet 66 and continuing to the right would be the space for additional equipment and the microwave 36.

It is important to maintain proper environmental conditions inside the laboratory and a combination humidistat, barometer and thermostat 62 is provided with the van. Additional slide storage 34 is also provided. Additional conveniences such as an angled footrest 70 and a food only refrigerator 68 are provided for the convenience of the pathologist utilizing the laboratory.

Figure 4A:
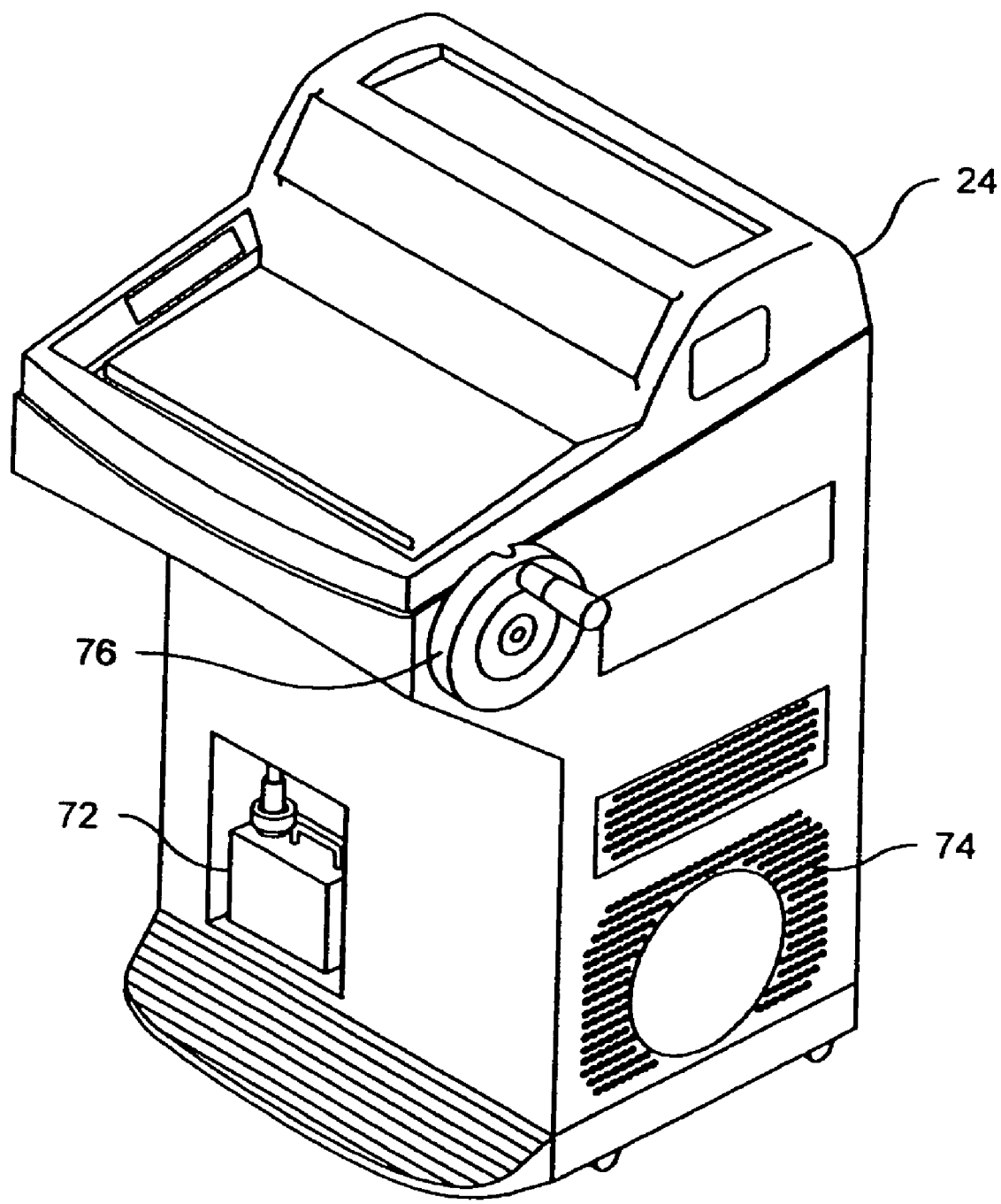
FIG. 4 is a front exposed view of the cryostat of the present invention.
FIG. 4b is an exposed view of the inside of the cryostat.
FIG. 4c is an exposed view of the cryostat knife.
Figure 4B:
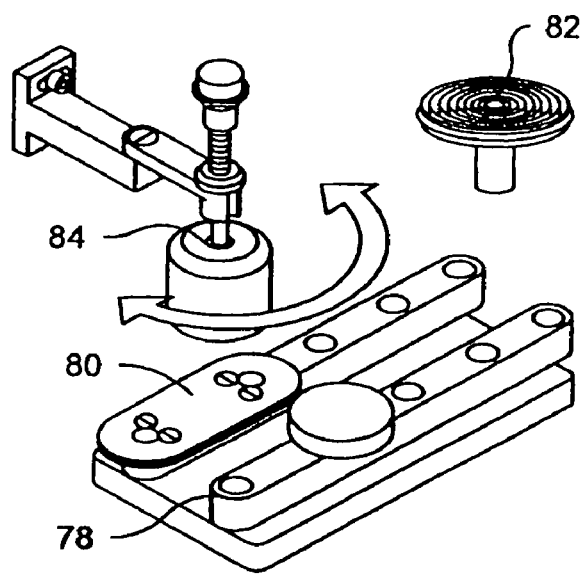
Figure 4C:
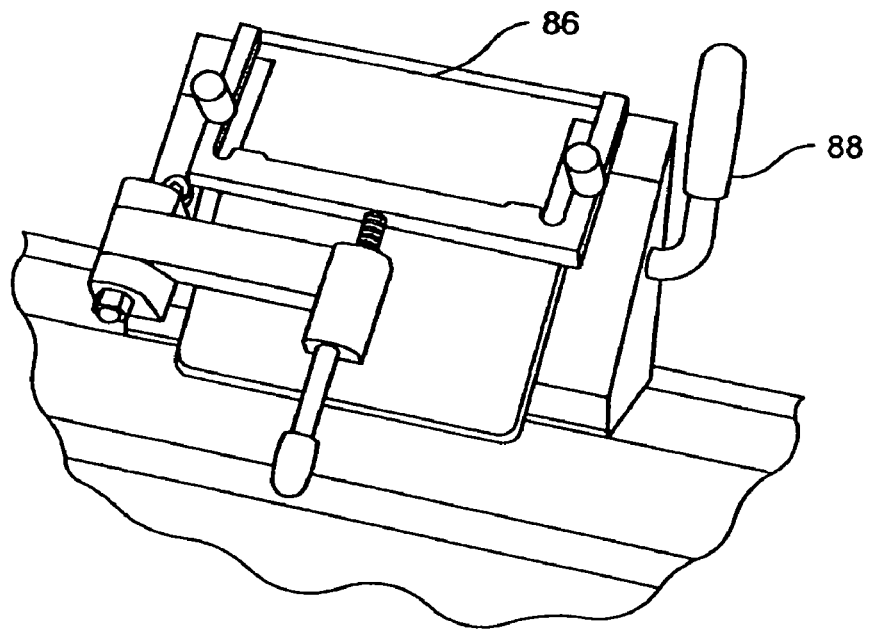

FIG. 4a shows the cryostat 24 and on the exterior of the cryostat the cryostat handle wheel 76, cryostat drainage bottle 72 and the cryostat vent 74. FIG. 4b is an exposed view of the inside of the cryostat and shows the chuck 82 which the tissue sample is placed on. The chuck 82 is placed on the chuck holder or freezing chamber 78 which is shown together with the quick freeze peltier 80. Additionally shown is the heat extractor 84 all of which combine to quickly freeze the tissue sample. Another important part of the cryostat 24 is the knife 86 as shown in FIG. 4c. The knife must be capable of cutting extremely thin sections of tissue and the physician operates the knife by use of the handle 88.

I claim:

1. A method for providing mobile intra-operative pathology consultation services to surgeons comprising:
    (a) obtaining a van containing a mobile intra-operative diagnosis laboratory having facilities for performing grossing, freezing, cutting, staining and microscopic diagnosis of fresh tissue specimens;
    (b) arranging to obtain fresh tissue specimens from said surgeons requiring intra-operative diagnosis;
    (c) transporting said mobile laboratory to a position to receive said fresh tissue specimens;
    (d) accepting said fresh tissue specimens;
    (e) making a microscopic diagnosis of said fresh tissue specimens;
    (f) communicating said diagnosis to said surgeons within twenty minutes of the time said fresh tissue specimens are accepted; and
    (g) maintaining proper environmental conditions within said laboratory for performing grossing, freezing, cutting, staining and microscopic diagnosis.

* * * * *